United States Patent
Roberts et al.

(10) Patent No.: US 9,943,708 B2
(45) Date of Patent: Apr. 17, 2018

(54) AUTOMATED CONTROL OF MICROMANIPULATOR ARM FOR HISTOTRIPSY PROSTATE THERAPY WHILE IMAGING VIA ULTRASOUND TRANSDUCERS IN REAL TIME

(75) Inventors: William W. Roberts, Saline, MI (US); Timothy L. Hall, Ann Arbor, MI (US); Charles A. Cain, Ann Arbor, MI (US); J. Brian Fowlkes, Ann Arbor, MI (US); Zhen Xu, Ann Arbor, MI (US); Michael Thomas Kusner, Jr., Perrysburg, OH (US); Dejan Teofilovic, Ann Arbor, MI (US)

(73) Assignees: HISTOSONICS, INC., Ann Arbor, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 523 days.

(21) Appl. No.: 12/868,768

(22) Filed: Aug. 26, 2010

(65) Prior Publication Data
US 2011/0054315 A1 Mar. 3, 2011

Related U.S. Application Data

(60) Provisional application No. 61/237,017, filed on Aug. 26, 2009.

(51) Int. Cl.
| | | |
|---|---|---|
| *A61B 8/00* | (2006.01) | |
| *A61N 7/00* | (2006.01) | |
| *A61N 7/02* | (2006.01) | |
| *A61B 8/12* | (2006.01) | |
| *A61B 34/00* | (2016.01) | |
| *A61B 17/22* | (2006.01) | |
| *A61B 90/50* | (2016.01) | |
| *A61B 90/00* | (2016.01) | |

(52) U.S. Cl.
CPC ............... *A61N 7/02* (2013.01); *A61B 8/12* (2013.01); *A61B 8/4218* (2013.01); *A61B 34/72* (2016.02);
(Continued)

(58) Field of Classification Search
CPC ........................................................ A61N 7/00
(Continued)

(56) References Cited

U.S. PATENT DOCUMENTS

| | | |
|---|---|---|
| 3,243,497 A | 3/1966 | Kendall et al. |
| 3,679,021 A | 7/1972 | Goldberg et al. |

(Continued)

FOREIGN PATENT DOCUMENTS

| | | |
|---|---|---|
| CN | 102481164 A | 5/2012 |
| DE | 3220751 A1 | 12/1983 |

(Continued)

OTHER PUBLICATIONS

Pulsed Cavitational Ultrasound Therapy for Controlled Tissue Homogenization, Parson et al. Ultrasound in Med. & Biol., vol. 32, No. 1, pp. 115-129, 2006.*

(Continued)

*Primary Examiner* — Serkan Akar
(74) *Attorney, Agent, or Firm* — Shay Glenn LLP (57) ABSTRACT

A medical imaging and therapy device is provided that may include any of a number of features. One feature of the device is that it can image a target tissue volume and apply ultrasound energy to the target tissue volume. In some embodiments, the medical imaging and therapy device is configured controllably apply ultrasound energy into the prostate by maintaining a cavitational bubble cloud generated by an ultrasound therapy system within an image of the prostate generated by an imaging system. The medical imaging and therapy device can be used in therapeutic applications such as Histotripsy, Lithotripsy, and HIFU, for example. Methods associated with use of the medical imaging and therapy device are also covered.

17 Claims, 6 Drawing Sheets

(52) U.S. Cl.
CPC ..... *A61B 90/50* (2016.02); *A61B 2017/22008* (2013.01); *A61B 2090/378* (2016.02)

(58) Field of Classification Search
USPC .................................................. 600/426, 429
See application file for complete search history.

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |

(56) References Cited

U.S. PATENT DOCUMENTS

| | | | |
|---|---|---|---|
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 8,333,115 B1 | 12/2012 | Garvey et al. |
| 9,526,923 B2 | 12/2016 | Jahnke et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1* | 4/2007 | Cain et al. ............ 600/439 |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1* | 10/2008 | Fichtinger et al. ........... 600/426 |
| 2008/0262486 A1 | 10/2008 | Zvuloni et al. |
| 2008/0312561 A1 | 12/2008 | Chauhan |
| 2008/0319356 A1 | 12/2008 | Cain et al. |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2010/0011845 A1 | 1/2010 | Laugharn et al. |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0305432 A1 | 12/2010 | Duhay et al. |
| 2010/0317971 A1 | 12/2010 | Fan et al. |
| 2011/0040190 A1 | 2/2011 | Jahnke et al. |
| 2011/0112400 A1 | 5/2011 | Emery et al. |
| 2011/0118602 A1 | 5/2011 | Weng et al. |
| 2011/0172529 A1 | 7/2011 | Gertner |
| 2011/0178444 A1 | 7/2011 | Slayton et al. |
| 2011/0257524 A1 | 7/2011 | Slayton et al. |
| 2011/0251528 A1 | 10/2011 | Canney et al. |
| 2011/0263967 A1 | 10/2011 | Bailey et al. |
| 2012/0010541 A1 | 1/2012 | Cain et al. |
| 2012/0029353 A1 | 2/2012 | Slayton et al. |
| 2012/0059264 A1 | 3/2012 | Hope Simpson et al. |
| 2012/0092724 A1 | 4/2012 | Pettis |
| 2012/0130288 A1 | 5/2012 | Holland et al. |
| 2012/0172720 A1 | 7/2012 | Kawabata |
| 2012/0189998 A1 | 7/2012 | Kruecker et al. |
| 2012/0271223 A1 | 10/2012 | Khanna |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0303906 A1 | 11/2013 | Cain et al. |
| 2014/0073995 A1 | 3/2014 | Teofilovic et al. |
| 2014/0100459 A1 | 4/2014 | Xu et al. |
| 2015/0258352 A1 | 9/2015 | Lin et al. |
| 2015/0375015 A1 | 12/2015 | Cain |
| 2016/0135916 A1 | 5/2016 | Rakic et al. |
| 2016/0184616 A1 | 6/2016 | Cain et al. |

FOREIGN PATENT DOCUMENTS

| | | |
|---|---|---|
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |

(56) References Cited

FOREIGN PATENT DOCUMENTS

| | | |
|---|---|---|
| EP | 0755653 A1 | 1/1997 |
| EP | 1374785 A1 | 1/2004 |
| EP | 1504713 A1 | 2/2005 |
| EP | 2397188 A1 | 12/2011 |
| GB | 2099582 A | 12/1982 |
| JP | 60-80779 A | 5/1985 |
| JP | 61-196718 A | 8/1986 |
| JP | HEI 2-215451 | 8/1990 |
| JP | HEI 6-197907 A | 7/1994 |
| JP | HEI 7-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | HEI 10-512477 | 12/1998 |
| JP | 2000300559 A | 10/2000 |
| JP | 2003-510159 A | 3/2003 |
| JP | 2004-505660 | 2/2004 |
| JP | 2005167058 A | 6/2005 |
| JP | 2007520307 A | 7/2007 |
| JP | 2010019554 A | 1/2010 |
| JP | 2010029650 A | 2/2010 |
| JP | 2010204068 A | 9/2010 |
| JP | 2004-512502 A | 4/2014 |
| WO | WO94/06355 A1 | 3/1994 |
| WO | WO 02/32506 A1 | 4/2002 |
| WO | WO2005/018469 A1 | 3/2005 |
| WO | WO 2007/035529 * | 3/2007 |
| WO | WO 2008/051484 | 5/2008 |
| WO | WO2011/040054 A1 | 7/2011 |
| WO | WO 2011/092683 A1 | 8/2011 |
| WO | WO2011/154654 A2 | 12/2011 |

OTHER PUBLICATIONS

Hall et al.; Imaging feedback of tissue liquefaction (histotripsy) in ultrasound surgery; IEEE Ultrasonic Symposium, Sep. 18-21, 2005, pp. 1732-1734.
Cain, Charles A.; Histrotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Parsons et al.; Pulsed cavitational ultrasound therapy for controlled tissue homogenization; Ultrasound in Med. & Biol.; vol. 32; pp. 115-129; 2006.
Roberts et al.; Pulsed cavitational ultrasound: a noninvasive technology for controlled tissue ablation (histotripsy) in the rabbit kidney; Journal of Urology; vol. 175; pp. 734-738; 2006.
Xu et al.; A new strategy to enhance cavitational tissue erosion by using a high intensity initiating sequence; IEEE Trans Ultrasonics Ferroelectrics and Freq Control; vol. 53; pp. 1412-1424; 2006.
Xu et al.; Controlled ultrasound tissue erosion: the role of dynamic interaction between insonation and microbubble activity; Journal of the Acoustical Society of America; vol. 117; pp. 424-435; 2005.
Xu et al.; Controlled ultrasound tissue erosion; IEEE Transaction on Ultrasonics, Ferroelectrics, and Frequency Control; vol. 51; pp. 726-736; 2004.
Xu et al.; Effects of acoustic parameters on bubble cloud dynamics in ultrasound tissue erosion (histotripsy); Journal of the Acoustical Society of America; vol. 122; pp. 229-236; 2007.
Xu et al.; High Speed Imaging of Bubble Clouds Generated in Pulsed Ultrasound Cavitational Therapy' Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31; pp. 1673-1682; 2005.
Xu et al.; Optical and acoustic monitoring of bubble cloud dynamics at a tissue-fluid interface in ultrasound tissue erosion; Journal of the Acoustical Society of America; vol. 121; pp. 2421-2430; 2007.

Cain et al.; U.S. Appl. No. 12/868,775 entitled "Devices and Methods for Using Controlled Bubble Cloud Cavitation in Fractionating Urinary Stones," filed Aug. 26, 2010.
Cain et al.; U.S. Appl. No. 12/887,705 entitled "Gel phantoms for testing cavitational ultrasound (histotripsy) transducers," filed Sep. 22, 2010.
Teofilovic, Dejan; U.S. Appl. No. 13/446,783 entitled "Systems and Methods for Obtaining Large Creepage Isolation on Printed Circuit Boards," filed Apr. 13, 2012.
Cain, Charles A.; U.S. Appl. No. 13/570,708 entitled "Lesion Generation Through Bone Using Histotripsy Therapy Without Aberration Correction," filed Aug. 9, 2012.
Appel et al.; Stereoscopic highspeed recording of bubble filaments; Ultrasonics Sonochemistry; vol. 11(1); pp. 39-42; Jan. 2004.
Atchley et al.; Thresholds for cavitation produced in water by pulsed ultrasound; Ultrasonics.; vol. 26(5); pp. 280-285; Sep. 1988.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Lauterborn et al.; Cavitation bubble dynamics studied by high speed photography and holography: part one; Ultrasonics; vol. 23; pp. 260-268; Nov. 1985.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roy et al.; A precise technique for the measurement of acoustic cavitation thresholds and some preliminary results; Journal of the Acoustical Society of America; vol. 78(5); pp. 1799-805; Nov. 1985.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sokolov et al.; Use of a dual-pulse lithotripter to generate a localized and intensified cavitation field; Journal of the Acoustical Society of America; vol. 110(3); pp. 1685-1695; Sep. 2001.
AVAGO Technologies; ACNV2601 High Insulation Voltage 10 MBd Digital Opotcoupler. Avago Technologies Data Sheet; pp. 1-11; Jul. 29, 2010.
Bjoerk et al.; Cool/MOS CP—How to make most beneficial use of the generation of super junction technology devices. Infineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan.

(56) References Cited

OTHER PUBLICATIONS 28, 2014] from the Internet: (http://web.archive.org/web/20110720091822/http://www.histotripsy.umich.edu/index.html>,entiredocument).
Hall et al.; Histotripsy of the prostate: dose effects in a chronic canine model; Urology; 74(4); pp. 932-937; Oct. 2009 (author manuscript).
Lake et al.; Histotripsy: minimally invasive technology for prostatic tissue ablation in an in vivo canine model; Urology; 72(3); pp. 682-686; Sep. 2008.
Bertolina et al.; U.S. Appl. No. 13/735,936 entitled "Histotripsy Therapy Transducer," filed Jan. 7, 2013.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clement et al.; A hemisphere array for non-invasive ultrasound brain therapy and surgery; Physics in Medicine and Biology, vol. 45, p. 3707-3719, Dec. 2000.
Desilets et al.; The Design of Efficient Broad-Band Piezoelectric Transducers; Sonics and Ultrasonics, IEEE Transactions on, vol. 25, pp. 115-125, May 1978.
Giannatsis et al.; Additive fabrication technologies applied to medicine and health care: a review; The International Journal of Advanced Manufacturing Technology; 40(1-2); pp. 116-127; Jan. 2009.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hartmann; Ultrasonic properties of poly(4-methyl pentene-1), Journal of Applied Physics, vol. 51, pp. 310-314, Jan. 1980.
Kim et al.; Dependence of particle volume fraction on sound velocity and attenuation of EPDM composites; Ultrasonics, vol. 46, pp. 177-183, Feb. 2007.
Krimholtz et al.; New equivalent circuits for elementary piezoelectric transducers; Electronics Letters, vol. 6, pp. 398-399, Jun. 1970.
Lensing et al.; Deep-vein thrombosis; The Lancet, vol. 353, pp. 479-485, Feb. 6, 1999.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-1599, Sep. 1996.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).
Yan et al.; A review of rapid prototyping technologies and systems; Computer-Aided Design, vol. 28, pp. 307-318, Apr. 1996.
Hall et al.; U.S. Appl. No. 13/874,083 entitled "Ultrasound Transducer Manufacturing Using Rapid-Prototyping Method," filed Apr. 30, 2013.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Emelianov et al.; Triplex ultrasound: Elasticity imaging to age deep venous thrombosis; Ultrasound Med Biol; 28(6); pp. 757-767; Jun. 2002.
Hynynen et al.; Tissue thermometry during ultrasound exposure; European Urology; 23(Suppl 1); pp. 12-16; 1993 (year of pub. sufficiently earlier than effective US filing date and any foreign priority date).
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Konofagou; Quo vadis elasticity imaging?; Ultrasonics; 42(1-9); pp. 331-336; Apr. 2004.
Kruse et al.; Tissue characterization using magnetic resonance elastography: Preliminary results; Phys. Med. Biol; 45(6); pp. 1579-1590; Jun. 2000.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Nightingale et al.; Analysis of contrast in images generated with transient acoustic radiation force; Ultrasound Med Biol; 32(1); pp. 61-72; Jan. 2006.
Okada et al.; A case of hepatocellular carcinoma treated by MR-guided focused ultrasound ablation with respiratory gating; Magn Reson Med Sci; 5(3); pp. 167-171; Oct. 2006.
Rowland et al.; MRI study of hepatic tumours following high intensity focused ultrasound surgery; British Journal of Radiology; 70; pp. 144-153; Feb. 1997.
Sapareto et al.; Thermal dose determination in cancer therapy; Int J Radiat Oncol Biol Phys; 10(6); pp. 787-800; Apr. 1984.

(56) References Cited

OTHER PUBLICATIONS

Souchon et al.; Visualisation of HIFU lesions using elastography of the human prostate in vivo: Preliminary results; Ultrasound Med. Biol; 29(7); pp. 1007-1015; Jul. 2003.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Zheng et al.; An acoustic backscatter-based method for localization of lesions induced by high-intensity focused ultrasound; Ultrasound Med Biol; 36(4); pp. 610-622; Apr. 2010.
AVTECH; AVR-8 Data sheet; May 23, 2004; 3 pages; retrieved from the internet (http//www.avtechpulse.com).
Avago Technologies; Avago's ACNV2601 optocoupler is an optically coupled logic gate; Data Sheet; 2 pages; Jul. 29, 2010.
Hobarth et al.; Color flow doppler sonography for extracorporal shock wave lithotripsy; Journal of Urology; 150(6); pp. 1768-1770; Dec. 1, 1993.
Maxwell et al.; In-vivo study of non-invasive thrombolysis by histotripsy in a porcine model; IEEE international Ultrasonics Symposium; IEEE; p. 220-223; Sep. 20, 2009.
Hall et al.; U.S. Appl. No. 15/583,852 entitled "Method of manufacturing an ultrasound system," filed May 1, 2017.
Cannata et al.; U.S. Appl. No. 14/323,693 entitled "Histotripsy excitation sequences optimized for bubble cloud formation using shock scattering," filed Jul. 3, 2014.
Wikipedia; Medical ultrasound; 15 pages; retrieved from the internet (https://en.wikipedia.org/w/index.php?title=Medical_utrasound&oldid=515340960) on Jan. 12, 2018.

\* cited by examiner

AUTOMATED CONTROL OF MICROMANIPULATOR ARM FOR HISTOTRIPSY PROSTATE THERAPY WHILE IMAGING VIA ULTRASOUND TRANSDUCERS IN REAL TIME

CROSS REFERENCE TO RELATED APPLICATIONS

This application claims the benefit under 35 U.S.C. 119 of U.S. Provisional Patent Application No. 61/237,017, filed Aug. 26, 2009, titled "MICROMANIPULATOR CONTROL ARM FOR THERAPEUTIC AND IMAGING ULTRASOUND TRANSDUCERS". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to imaging and treating tissue with ultrasound devices. More specifically, the present invention relates to imaging and ablating tissue with Histotripsy devices.

BACKGROUND OF THE INVENTION

Histotripsy and Lithotripsy are non-invasive tissue ablation modalities that focus pulsed ultrasound from outside the body to a target tissue inside the body. Histotripsy mechanically damages tissue through cavitation of micro bubbles which homogenizes cellular tissues into an a-cellular liquid that can be expelled or absorbed by the body, and Lithotripsy is typically used to fragment urinary stones with acoustic shockwaves.

Histotripsy is the mechanical disruption via acoustic cavitation of a target tissue volume or tissue embedded inclusion as part of a surgical or other therapeutic procedure. Histotripsy works best when a whole set of acoustic and transducer scan parameters controlling the spatial extent of periodic cavitation events are within a rather narrow range. Small changes in any of the parameters can result in discontinuation of the ongoing process.

Histotripsy requires high peak intensity acoustic pulses which in turn require large surface area focused transducers. These transducers are often very similar to the transducers used for Lithotripsy and often operate in the same frequency range. The primary difference is in how the devices are driven electrically.

Histotripsy pulses consist of a (usually) small number of cycles of a sinusoidal driving voltage whereas Lithotripsy is (most usually) driven by a single high voltage pulse with the transducer responding at its natural frequencies. Even though the Lithotripsy pulse is only one cycle, its negative pressure phase length is equal to or greater than the entire length of the Histotripsy pulse, lasting tens of microseconds. This negative pressure phase allows generation and continual growth of the bubbles, resulting in bubbles of sizes up to 1 mm. The Lithotripsy pulses use the mechanical stress produced by a shockwave and these 1 mm bubbles to cause tissue damage or fractionate stones.

In comparison, each negative and positive cycle of a Histotripsy pulse grows and collapses the bubbles, and the next cycle repeats the same process. The maximal sizes of bubbles reach approximately tens to hundreds of microns. These micron size bubbles interact with a tissue surface to mechanically damage tissue.

In addition, Histotripsy delivers hundreds to thousands of pulses per second, i.e., 100-1 kHz pulse repetition frequency. Lithotripsy only works well within a narrow range of pulse repetition frequency (usually 0.5-1 Hz). Studies show that the efficacy and efficiency of lithotripsy decreases significantly when the pulse repetition frequency is increased to 10-100 Hz. The reduced efficiency is likely due to the increased number of mm size bubbles blocking the shock waves and other energy from reaching the stone.

Histotripsy typically comprises delivering acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle between approximately 0.1% and 5% and in some embodiments less than 5%, and a pulse repetition frequency of less than 5 KHz.

Diagnostic ultrasound can be used during Histotripsy procedures to visualize the surgical anatomy and monitor the process in real time. The Histotripsy cavitation bubble cloud can appear very clearly on diagnostic ultrasound as a hyperechoic (light) region and ablated homogenized tissue can appear as a hypoechoic (dark) region. Large and irregular tissue volumes can be ablated using Histotripsy by electronically changing the focus of a therapeutic array or by mechanically moving the focus of the therapeutic transducer within the surgical target area.

SUMMARY OF THE INVENTION

The present invention relates to an imaging and therapy system comprising a micro-manipulator system, an ultrasound therapy system supported by the micro-manipulator system, and an imaging system supported by the micro-manipulator system apart from the ultrasound therapy system, the micro-manipulator system being adapted and configured to maintain a focal point of the ultrasound therapy system within a field of view of the imaging system.

In some embodiments, the micro-manipulator is adapted and configured to position the imaging system within a rectum of a human male patient and to position the ultrasound therapy system in acoustic contact with a perineum of the patient while the imaging system is in the rectum. In one embodiment, the imaging system comprises a trans-rectal probe.

In some embodiments, the focal point of the ultrasound therapy system is approximately 0.8 cm to 4 cm from the imaging system.

In many embodiments of the imaging and therapy system, the ultrasound therapy system comprises a histotripsy system. The ultrasound therapy system can comprise an ultrasound therapy transducer configured to generate cavitational micro bubbles in tissue. In some embodiments, the ultrasound therapy system comprises an ultrasound therapy transducer configured to deliver acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle of less than 5% and in some embodiments less than 5%, and a pulse repetition frequency of less than 5 KHz.

In some embodiments, the micro-manipulator system comprises a robotic arm. The robotic arm can move in up to six degrees of freedom, for example. In another embodiment, the micro-manipulator system comprises at least four stepper motors configured to move the micro-manipulator system in up to four degrees of freedom. In one embodiment, one of the at least four stepper motors is configured to rotate the imaging system along a roll axis. In another embodiment, one of the at least four stepper motors is configured to rotate the ultrasound therapy system along a pitch axis. In yet another embodiment, one of the at least four stepper motors is configured to rotate the ultrasound therapy system along a yaw axis. In an additional embodiment, one of the at least four stepper motors is configured to advance the ultrasound therapy system along a forward/back axis.

In some embodiments, the imaging and therapy system can further comprise a control system configured to automatically control the micro-manipulator system to maintain the focal point of the ultrasound therapy system within the field of view of the imaging system. The control system can include a controller, such as a computer, as well as an input device and a display.

Methods of using an imaging and therapy device are also provided. In one embodiment, a method of ablating tissue in a prostate of a patient comprises supporting an imaging system and an ultrasound therapy system on micro-manipulator system, inserting the imaging system into the patient's rectum, generating an image of the prostate with the imaging system, and controllably applying ultrasound energy from the ultrasound therapy system into the prostate by maintaining a bubble cloud generated by the ultrasound therapy system within the image of the prostate generated by the imaging system.

In some embodiments, the method further comprises placing the ultrasound therapy system in acoustic contact with the patient's perineum.

In another embodiment, the method further comprises maintaining the bubble cloud generated by the ultrasound therapy system within approximately 0.8 cm to 4 cm of the imaging system.

In an additional embodiment, the controllably applying ultrasound energy step comprises controllably applying Histotripsy therapy. In another embodiment, the controllably applying ultrasound energy step comprises delivering acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle of less than 5% and in some embodiments less than 5%, and a pulse repetition frequency of less than 5 KHz. In another embodiment, the controllably applying ultrasound energy step further comprises automatically maintaining the bubble cloud generated by the ultrasound therapy system within the image of the prostate generated by the imaging system with a control system.

In some embodiments, the method further comprises mechanically damaging tissue in the prostate. The method can further comprise mechanically damaging tissue in the prostate to treat BPH. In an additional embodiment, the method comprises mechanically damaging tissue in the prostate to treat prostate cancer.

In one embodiment, the method comprises rotating the imaging system to create a 3D image of the prostate.

DETAILED DESCRIPTION OF THE INVENTION

Histotripsy may be used to ablate or damage tissue for treatment of a variety of disorders. Particularly, Histotripsy can be used to ablate tissue for the treatment of benign prostate hyperplasia (BPH) and prostate cancer. In one Histotripsy system, an imaging system and an ultrasound therapy system are held and positioned by an electromechanical micro-manipulator system. The micro-manipulator system can be attached to a procedure table or can be held above the procedure table and secured to the ceiling. In some embodiments, the micro-manipulator system can be joystick controlled or controlled by a computer tracking and positioning program. A trans-rectal (TR) ultrasound imaging system can be inserted in the patient's rectum to confirm accurate targeting and localization of the bubble cloud formed by the therapy system during treatment, and for imaging of target tissue during the Histotripsy procedure. The imaging system can be attached to the micro-manipulator system and repositioned axially and rotated radially during the procedure to image and track therapy.

One aspect of the invention provides a new micro-manipulator system and method of use for therapeutic and imaging systems in the fields of Histotripsy, Lithotripsy, or HIFU tissue ablation. The micro-manipulator system can be a small, portable and easy to use system and can include attachment points for both an ultrasound therapy system and an imaging system. The micro-manipulator system can be configured to independently control movement of both the therapy system and the imaging system.

Figure 1:
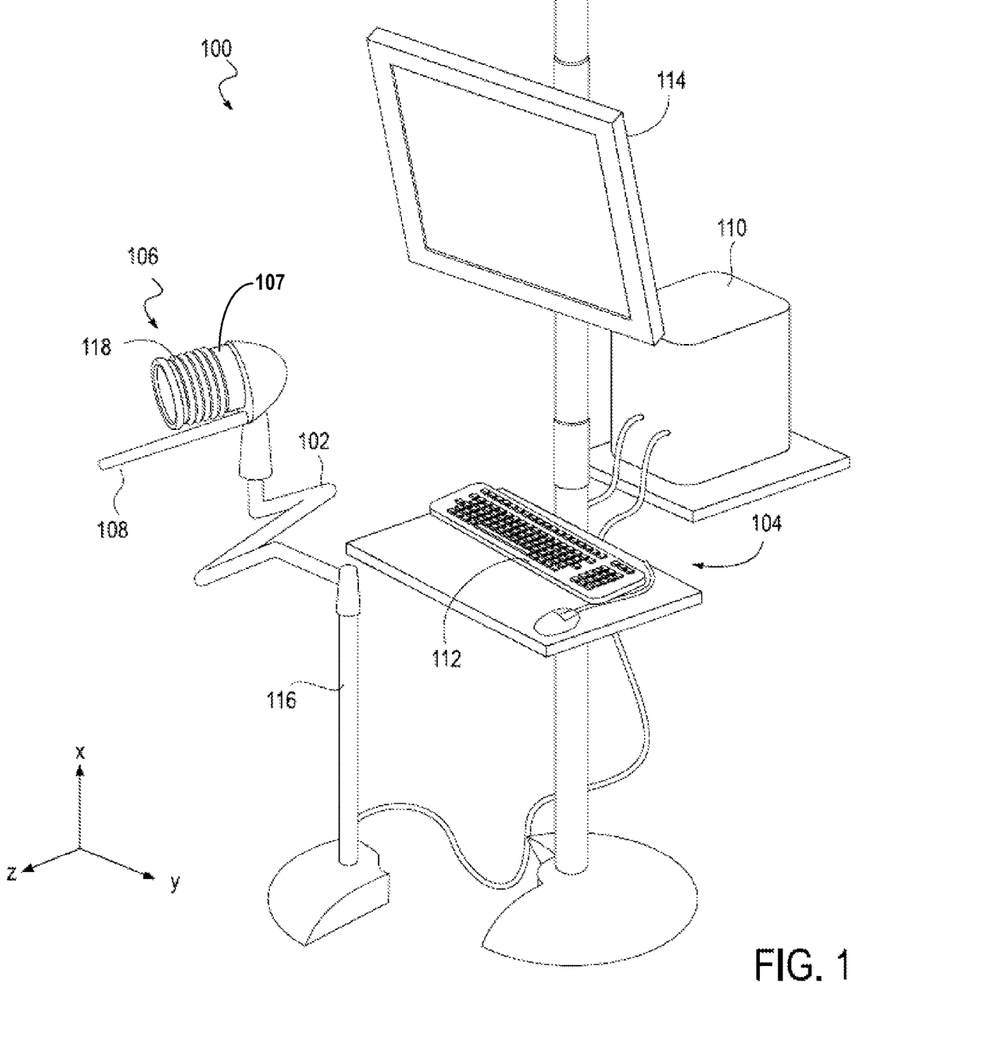
FIG. 1 illustrates one embodiment of an imaging and therapy system including a micro-manipulator system.

Referring now to FIG. 1, imaging and therapy system 100 can comprise micro-manipulator system 102, control system 104, ultrasound therapy system 106, and imaging system 108. Micro-manipulator system 102 can be adapted and configured to attach to and move the ultrasound therapy system 106 in up to six degrees of freedom (e.g., forward/back, left/right, up/down, yaw, pitch, and roll in the x, y, and z planes shown in FIG. 1). It should be understood that some systems may not require all six degrees of freedom of movement. The micro-manipulator system can also be configured to attach to and move the imaging system in up to six degrees of freedom, however, typically only the forward/back and roll degrees of freedom are required for the imaging system. In some embodiments, the micro-manipulator system comprises a robotic arm with up to six degrees of freedom. The robotic arm can be configured to hold the weight of both the imaging system and the ultrasound therapy system steady during positioning and treatment. In the embodiment of FIG. 1, micro-manipulator system 102 is attached to a separate mobile stand 116. Alternatively, the micro-manipulator system can be mounted on a procedure table (not shown).

Control system 104 can include controller 110, input device 112, and display 114. The controller can be a computer having hardware and software configured to control movement of the micro-manipulator system. For example, the controller can comprise a CPU, memory, operating system, and other computing essentials required to load software and control attached hardware. The input device 112 can be a keyboard and mouse or a joystick, for example. Display 114 can be, for example, an electronic display or a graphical user interface (GUI).

Ultrasound therapy system 106 can comprise an ultrasound therapy transducer 107 or transducers configured to deliver ultrasound energy to a target tissue volume. In some embodiments, the ultrasound therapy transducer 107 can be a Histotripsy ultrasound transducer configured to generate cavitational micro bubbles in tissue. In some embodiments, the Histotripsy ultrasound transducer can be configured to deliver acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle between approximately 0.1% and 5% and in some embodiments less than 5%, and a pulse repetition frequency of less than 5 KHz. In other embodiments, the ultrasound therapy system 106 can comprise a Lithotripsy ultrasound transducer or a HIFU transducer. The ultrasound therapy system 106 can include a coupling mechanism 118 for acoustically coupling the transducer 107 to a patient, such as a bellows. Alternatively, the coupling mechanism can be separate from the ultrasound therapy system and attached to the patient instead. Several embodiments of a suitable coupling mechanism are described in U.S. patent application Ser. No. 12/858,242, filed Aug. 17, 2010, titled "Disposable Acoustic Coupling Medium Container".

In some embodiments, the imaging system 108 is configured to image the target tissue volume and comprises a C-mode diagnostic ultrasound imaging system. In some embodiments, the imaging system can be a trans-rectal imaging probe. The imaging system can be configured to image tissue in 2D or 3D. In some embodiments, a trans-rectal imaging probe can be configured to be inserted into the rectum of a patient to image the prostate and surrounding tissues. In other embodiments, a secondary imaging transducer may be held in the center of the ultrasound therapy system 106.

Figure 2A:
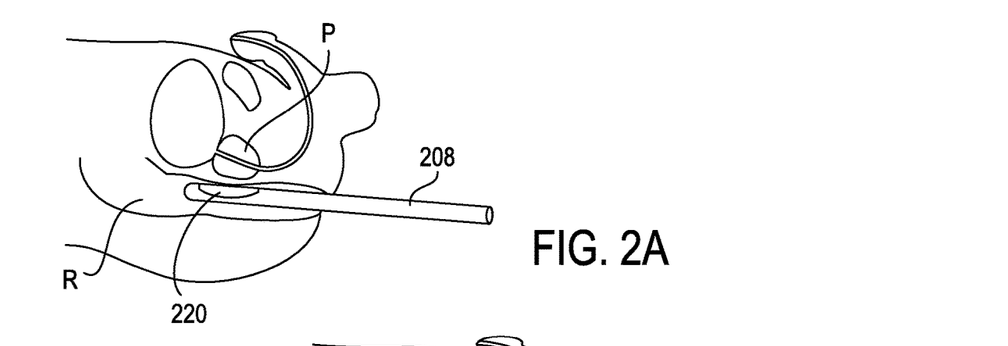
FIGS. 2A-2B illustrate an imaging system inside a patient.
Figures 2B, 3A:
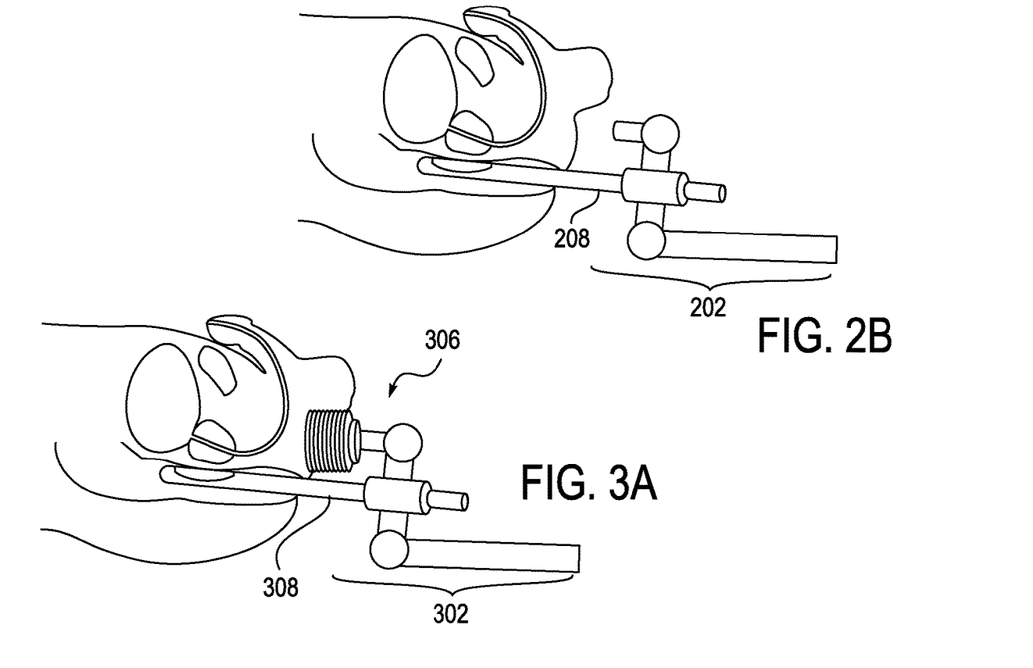
FIGS. 3A-3B and 4A-4B illustrate an imaging system and a therapeutic ultrasound transducer attached to a micro-manipulator system.

Methods of using a imaging and therapy system will now be described. FIG. 2A illustrates an imaging system 208 inserted in the rectum R of a patient. Imaging transducer 220 of imaging system 208 can be positioned adjacent to the prostate P of the patient. FIG. 2B illustrates the imaging system 208 coupled to a micro-manipulator system 202, such as the micro-manipulator system described above. In some embodiments, the imaging system and the micro-manipulator system can be positioned manually at the beginning of the procedure. In some embodiments, the imaging system 208 can be positioned in the rectum, as shown in FIG. 2A, then the micro-manipulator system can be positioned and attached to the imaging system, as shown in FIG. 2B. The imaging system can be advanced in the rectum so that its imaging aperture defined by imaging transducer 220 is adjacent to the prostate and is configured to acquire an image of the prostate in the transverse plane. The imaging system can also be positioned by rotating radially along the longitudinal axis of the probe so as to acquire an image of the prostate in the medial sagittal plane.

Figure 3B:
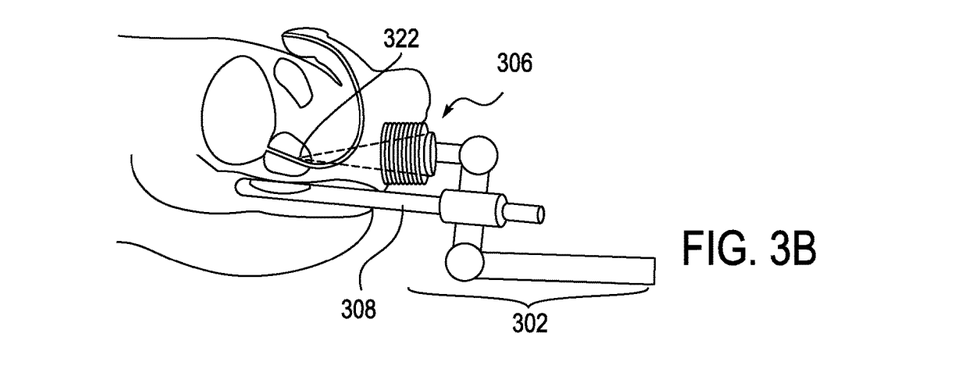

As shown in FIGS. 3A-B, ultrasound therapy system 306 can mount on micro-manipulator system 302 such that it is facing the perineal region between the anus and scrotum of the patient. Thus, referring to FIG. 3B for treatment of the prostate, the ultrasound therapy system can be positioned so as to locate the focal point 322 of the ultrasound therapy system 306 within the field of view of the imaging system 308 and within the prostate to be treated. In FIGS. 3A-3B, the micro-manipulator system is adapted and configured to position the imaging system within a rectum of the patient and to position the ultrasound therapy system in acoustic contact with the perineum while the imaging system is in the rectum.

Figure 4A:
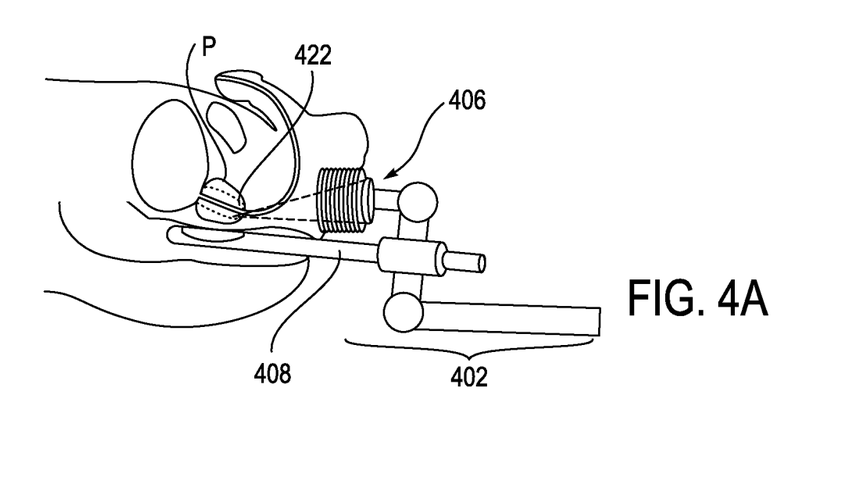
Figure 4B:
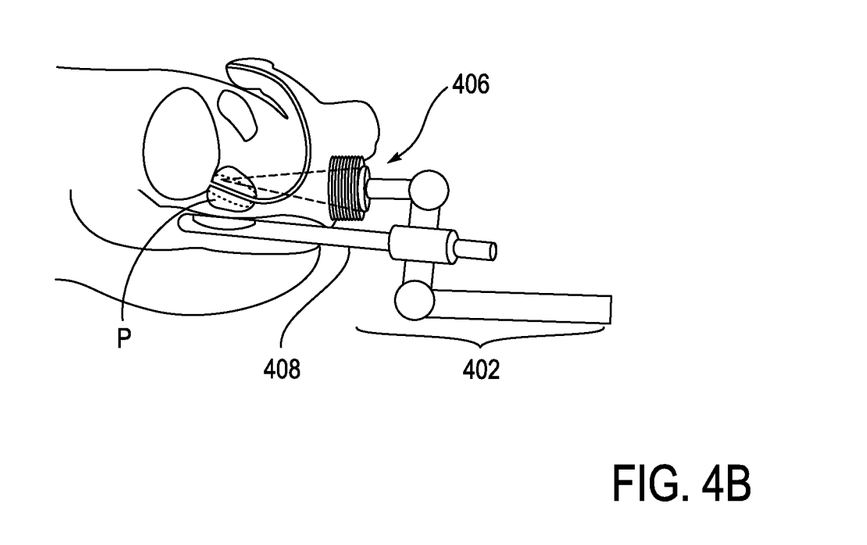

Movement of the micro-manipulator system, imaging of the target tissue with the imaging system, and treatment of the target tissue with the ultrasound therapy system can be managed, observed, and controlled with a control system, such as control system 104 described above and illustrated in FIG. 1. Referring now to FIGS. 4A-B and FIG. 1, the initial positioning of focal point 422 can be established mechanically by the micro-manipulator system 402. As shown in FIG. 4A, ultrasound therapy system 406 can be moved by micro-manipulator system 402 to position focal point 422 on target tissues in the prostate P and within the field of view of the imaging system. The micro-manipulator system is configured to position the focal point 422 on one or both lobes of the prostate, as shown in FIGS. 4A-B.

The micro-manipulator system 402 can be manually positioned by the user, such as a physician, by using input device 112 while under visual guidance from an imaging system 108 and display 114 of FIG. 1. In other embodiments, the micro-manipulator system can also be positioned automatically with a controller, such as controller 110 of FIG. 1. The controller can be programmed with software and/or hardware according to a surgical plan to automatically position and move the micro-manipulator system and the ultrasound therapy system to locate the focal point in the target tissue and ablate the desired tissues within the target tissue volume.

Figure 5:
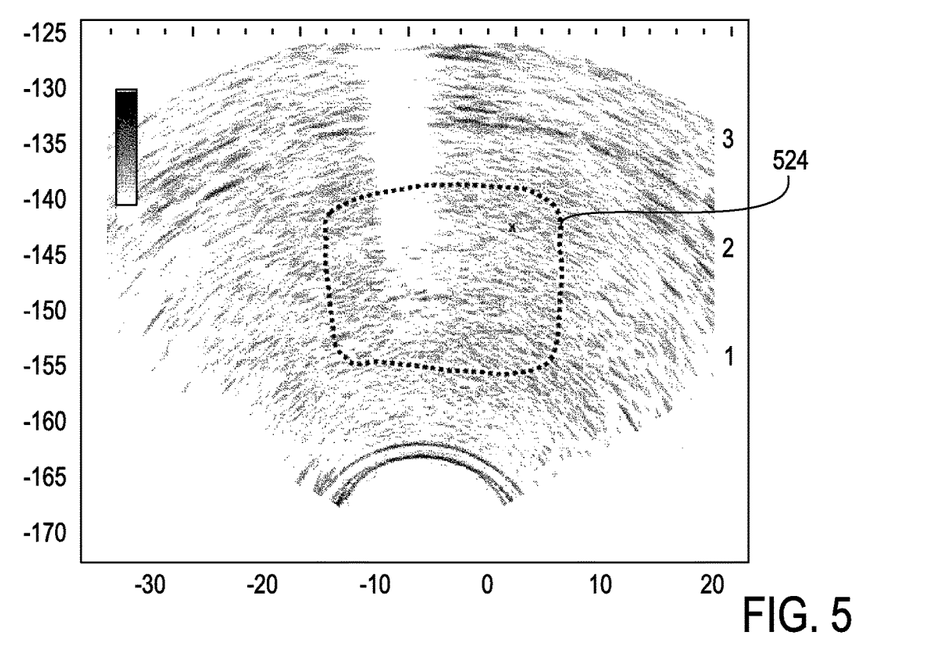
FIG. 5 is an ultrasound image of tissue damaged with a Histotripsy procedure.

Referring still to FIG. 1, the imaging system 108 can be integrated with the ultrasound therapy system 106 and control system 104 for surgical planning. Surgical planning can be facilitated by acquiring multiple transverse or sagittal images of the target tissue volume, such as the prostate, with imaging system 108, and storing these images in controller 110 of control system 104. In some embodiments, scanned images can be spaced approximately 1-10 mm apart. These images can be stored in the controller 110 and inputted into surgical planning software within the controller. The images can retrieved by the surgical planning software, and the treatment area can then be drawn or marked on each image to identify a desired ablation volume, as illustrated by the ablation volume 524 outlined in FIG. 5.

In other embodiments, scanning the target tissue volume can comprise rotating the imaging system through the sagittal (longitudinal) plane to acquire images through the entire volume in order to reconstruct a three-dimensional (3D) image of the target tissue volume. Transverse or sagittal plane images can then be acquired and examined by the user or the control system for detailed surgical planning. The treatment volume can be drawn or marked on the image, as described above.

In some embodiments, the surgical planning software or the user can create a surgical plan within the target tissue volume, such as within the prostate, with subsequent treatment volumes separated by 1 mm increments (e.g., total range 0.2 mm-1 cm). Each treatment target can be assigned a different dose of ultrasound therapy. The ultrasound dose can be determined, e.g., by the number of pulses delivered or the treatment duration in each treatment target. In some embodiments, the ultrasound therapy comprises Histotripsy therapy. Histotripsy can be performed within the planned treatment volume. The treatment can be tracked on the control system display, which can also display the images from the imaging system. In some embodiments, the focal point of the ultrasound therapy transducer can be automatically moved by the micro-manipulator system through the surgical treatment volume (e.g., of the prostate) to ablate the treatment volume under real time imaging from the imaging system. In some embodiments, the ultrasound therapy system is configured to ablate or mechanically damage the treatment volume. The ultrasound therapy system can be configured to ablate or mechanically damage tissue of the prostate to treat BPH or prostate cancer, for example.

In some embodiments, the initial default position of the imaging system is in the middle of the prostate, and the initial default position of the ultrasound therapy system focal point is within the transverse and sagittal field of view of the imaging system. In some embodiments, the default positions of the imaging and therapy systems may be re-established by pressing a default control element (e.g., a button or a key) on the control system.

Referring still to FIGS. 4A-B and FIG. 1, the imaging system 408 can be advanced and rotated manually during a Histotripsy procedure to keep the cavitational bubble cloud in the imaging field and to facilitate real time monitoring. Alternatively, the control system can automatically position the micro-manipulator system, imaging system, and the ultrasound therapy system to keep the cavitational bubble cloud in the imaging field. For example, the micro-manipulator system can be rotated and/or advanced in the axial direction automatically by the control system to a degree that is calculated based on the movement of the therapy system and the field of view of the imaging system. As another alternative, imaging feedback can be used to guide the rotation of the imaging system. The imaging system can rotate for small steps, until the imaging feedback indicates a hyperechoic zone (i.e., high backscatter amplitude) in the treatment region, which would indicate a Histotripsy cavitation bubble cloud.

In some embodiments, the ultrasound therapy system can generate an ultrasonically induced cavitation bubble cloud in a tissue volume using pulsed ultrasound at a frequency of between about 100 kHz and about 5 MHz having high amplitude pressure waves with peak negative pressure above 5 MPa, an ultrasound pulse duration of 1-1000 cycles, a pulse repetition frequency of less than about 5 kHz and a duty cycle less than about 5%.

In other embodiments, the focused ultrasound therapy transducer generates an ultrasonically induced cavitation bubble cloud in a tissue volume using an ultrasound frequency between about 250 kHz and about 1.5 MHz, high amplitude pressure waves with intensities exceeding 2000 W/cm$^2$ and peak positive pressure above 20 MPa (such as, e.g., between 30 MPa and 500 MPa) and peak negative pressure less than 5 MPa (such as, e.g., between 5 MPa and 40 MPa), ultrasound pulse duration of less than 30 cycles (such as, e.g., between 0.2 µs and 30 µs (1 to 20 cycles)), a pulse repetition frequency of less than about 5 kHz and a duty cycle less than about 5%.

Figure 6A:
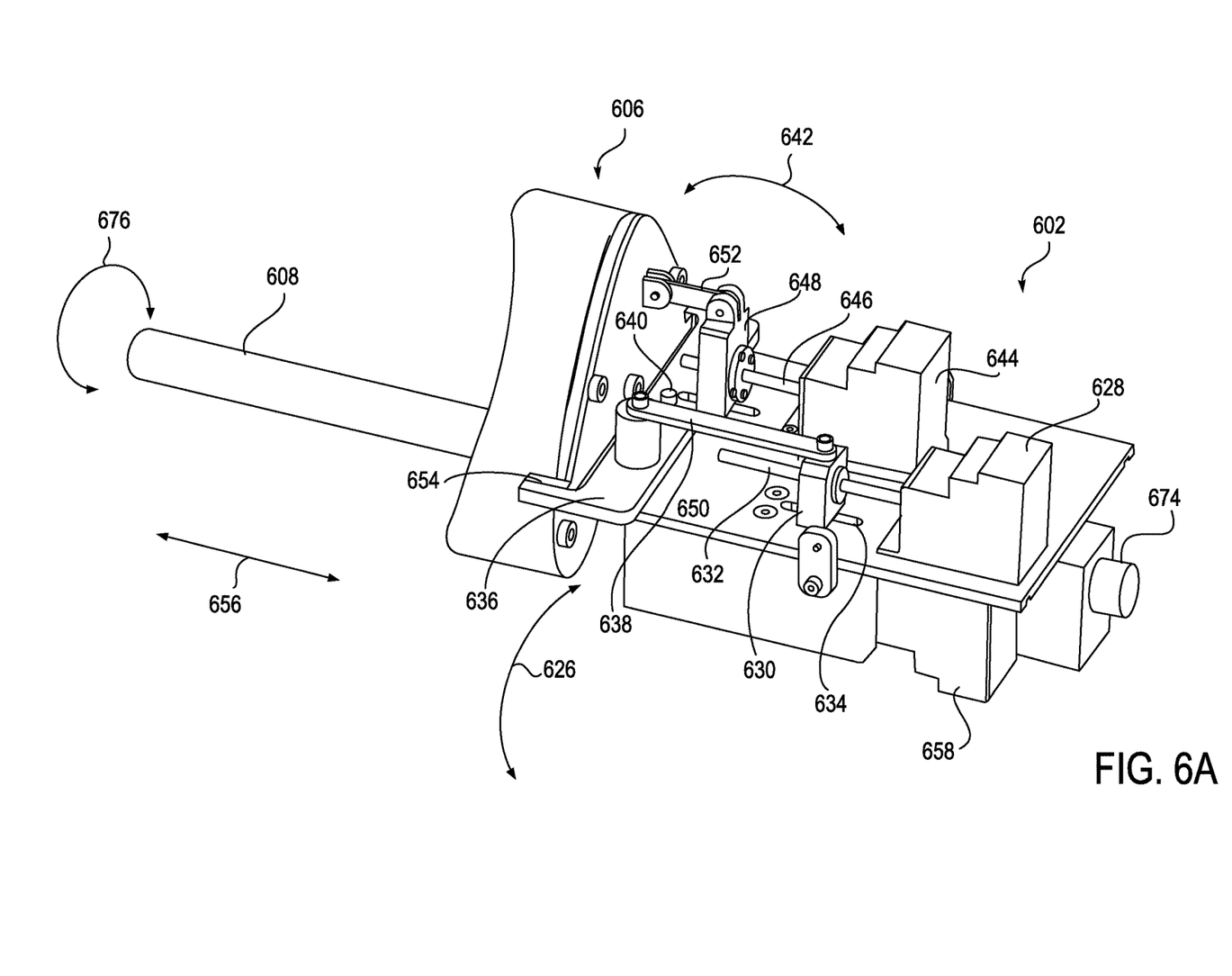
FIGS. 6A-6B are two views of a micro-manipulator system.
Figure 6B:
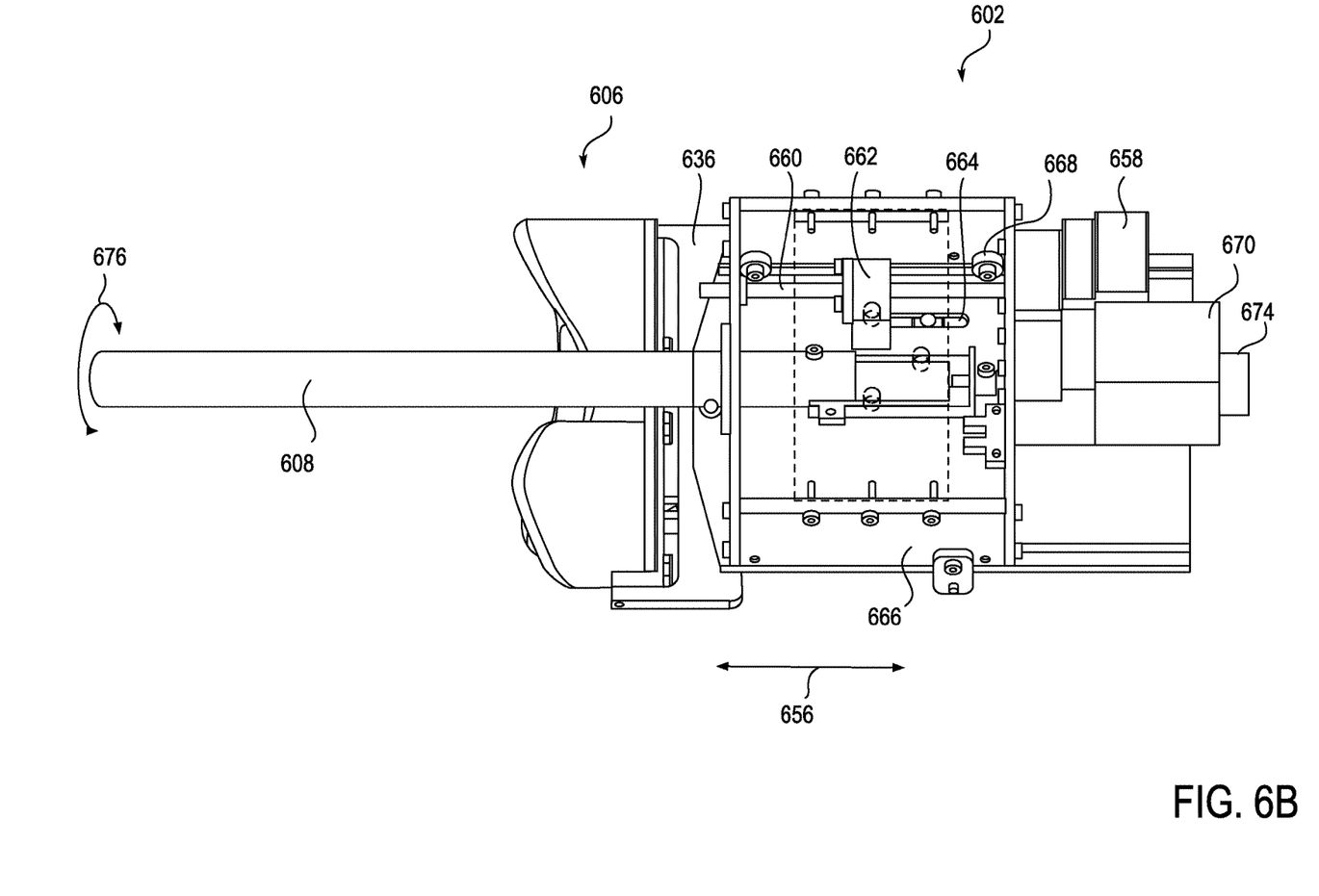

FIGS. 1-4 above described and illustrated the micro-manipulator system as a robotic arm. However, FIGS. 6A-B illustrate an alternative embodiment of a micro-manipulator system 602. As described above, ultrasound therapy system 606 and imaging system 608 can be attached to the micro-manipulator system. The micro-manipulator system as shown in FIG. 6A can be configured to move the ultrasound therapy system 606 in up to three degrees of freedom (e.g., forward/back, yaw, and pitch) and can be configured to move the imaging system 608 in one degree of freedom (e.g., roll). The micro-manipulator system 602 of FIGS. 6A-B can further be automatically controlled by a control system, such as control system 104 of FIG. 1, to automatically position and control the ultrasound therapy system and the imaging systems described herein.

To achieve rotation along the yaw axis, defined by arrow 626, stepper motor 628 can be attached to slide-block 630 with screw rod 632. The screw rod and slide-block can include mating external and internal threading, respectively. When stepper motor 628 rotates screw rod 632, the threading of screw rod causes slide-block to move linearly along slot 634. Slide-block 630 can be attached to rotation tray 636 with connecting rod 638. The connecting rod can be attached to rotation tray at a position away from rotation pin 640 of the tray. When slide-block moves linearly along slot 634, connecting rod 638 pushes against rotation tray 636, causing the tray, and thus the ultrasound therapy system 606, to rotate in the yaw axis around rotation pin 640.

The micro-manipulator system can achieve rotation along the pitch axis, defined by arrow 642, in a similar manner. In FIG. 6A, stepper motor 644 can rotate screw rod 646, causing slide-block 648 to move linearly in slot 650. This can cause connecting rod 652 to push against ultrasound therapy system 606 to rotate in the pitch axis around rotation pins 654.

The micro-manipulator system can achieve movement along the forward/back axis, defined by arrow 656, in a similar manner. In FIGS. 6A-6B, stepper motor 658 can rotate screw rod 660, causing slide-block 662 to move linearly in slot 664. Slide-block 662 can be attached to frame 666, which is attached to ultrasound therapy system 606. Thus, linear movement of the slide block can cause the frame to move linearly along wheels 668, thereby advancing ultrasound therapy system 606 in the forward/back direction 656.

The micro-manipulator system can achieve movement of the imaging system 608 in the roll axis, defined by arrow 676 in a similar manner. Stepper motor 670 can be attached directly to imaging system 608 with screw rod 672. Stepper motor 670 can rotate screw rod 672, causing rotation of imaging system 606. The stepper motor 670 may further include knob 674 to allow for manual rotation of imaging system 608.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An imaging and therapy system comprising:
a micro-manipulator system;
an ultrasound therapy system supported by the micro-manipulator system, the ultrasound therapy system comprises a histotripsy system that is configured to generate a cavitation bubble cloud in a target tissue volume; and
an imaging system supported by the micro-manipulator system apart from the ultrasound therapy system and configured to monitor the cavitation bubble cloud in the target tissue volume in real time;
wherein the micro-manipulator system comprises a control system configured to automatically position and move the imaging system and the ultrasound therapy system, wherein the control system is further configured to locate a focal point of the ultrasound therapy system which is positioned a distance of 0.8 cm to 4 cm from the imaging system and further configured to ablate desired tissue within the target tissue volume by retrieving images from the imaging system and identify a desired treatment volume; and
wherein the control system comprises a computer that is configured to independently control relative movement of the ultrasound therapy system and the imaging system, and further configured to automatically maintain the cavitation bubble cloud generated by the ultrasound therapy system within a field of view of the imaging system;
wherein the micro-manipulator is adapted and configured to position the imaging system within a return of a human male patient and further configured to position the ultrasound therapy system in acoustic contact with a perineum of the patient while the imaging system is in the rectum; and
wherein the ultrasound therapy system comprises an ultrasound therapy transducer configured to deliver acoustic pulses that is configured to operate at a frequency between 50 KHz and 5 MHz, having a pulse intensity with a peak negative pressure between 8 MPa to 40 MPa, a peak positive pressure between 10 MPa to 500 MPa, a pulse length shorter than 50 cycles, a duty cycle of less than 5%, and a pulse repetition frequency between 100 hz to 5 KHz.

2. The imaging and therapy system of claim 1 wherein the ultrasound therapy system comprises an ultrasound therapy transducer configured to generate cavitational micro bubbles in tissue.

3. The imaging and therapy system of claim 1 wherein the imaging system comprises a trans-rectal probe.

4. The imaging and therapy system of claim 1 wherein the micro-manipulator system comprises a robotic arm.

5. The imaging and therapy system of claim 4 wherein the robotic arm can move in up to six degrees of freedom.

6. The imaging and therapy system of claim 1 wherein the micro-manipulator system comprises at least four stepper motors configured to move the micro-manipulator system in up to four degrees of freedom.

7. The imaging and therapy system of claim 6 wherein one of the at least four stepper motors is configured to rotate the imaging system along a roll axis.

8. The imaging and therapy system of claim 6 wherein one of the at least four stepper motors is configured to rotate the ultrasound therapy system along a pitch axis.

9. The imaging and therapy system of claim 6 wherein one of the at least four stepper motors is configured to rotate the ultrasound therapy system along a yaw axis.

10. The imaging and therapy system of claim 6 wherein one of the at least four stepper motors is configured to advance the ultrasound therapy system along a forward/back axis.

11. The imaging and therapy system of claim 1 further comprising a control system configured to automatically control the micro-manipulator system to maintain the cavitation bubble cloud generated by the ultrasound therapy system within the image generated by the imaging system.

12. A method of ablating tissue in a patient with a micro-manipulator system, comprising:
inserting an imaging system of the micro-manipulator system into the patient's rectum;
generating one or more images of a target tissue volume with the imaging system;
delivering ultrasound energy from an ultrasound therapy system comprises applying histotripsy therapy of the micro-manipulator system into the target tissue volume to generate a cavitation bubble cloud in the target tissue volume, wherein images of the target tissue volume retrieved from the imaging system and desired treatment volume identified from the images;
providing a controller system comprising a computer for;
monitoring the cavitation bubble cloud with the imaging system in real time; and
automatically moving the micro-manipulator system to locate a focal point of the ultrasound therapy system with the imaging system
the movement step further comprises controlling movement of the imaging system and the ultrasound therapy system to maintain the cavitation bubble cloud generated by the ultrasound therapy system within a distance of 0.8 cm to 4 cm of the imaging system; and
independently controlling relative movement of the ultrasound therapy system and the imaging system so as to automatically maintain the cavitation bubble cloud generated by the ultrasound therapy system within a field of view of the imaging system;
wherein the applying ultrasound therapy step comprises delivering acoustic pulses that operate at a frequency between 50 KHz and 5 MHz, having a pulse intensity with a peak negative pressure between 8 MPa to 40 MPa, a peak positive pressure between 10 MPa to 500 MPa, a pulse length shorter than 50 cycles, a duty cycle of less than 5%, and a pulse repetition frequency between 100 hz to 5 KHz.

13. The method of claim 12 further comprising placing the ultrasound therapy system in acoustic contact with the patient's perineum.

14. The method of claim 12 further comprising mechanically damaging tissue in the prostate.

15. The method of claim 14 further comprising mechanically damaging tissue in the prostate to treat benign prostatic hyperplasia.

16. The method of claim 14 further comprising mechanically damaging tissue in the prostate to treat prostate cancer.

17. The method of claim 14 further comprising rotating the imaging system to create a 3D image of the prostate.

* * * * *